(12) United States Patent
Lowery

(10) Patent No.: US 8,219,168 B2
(45) Date of Patent: Jul. 10, 2012

(54) ARTICLE AND METHOD FOR APPLYING A COUPLING AGENT FOR A NON-INVASIVE OPTICAL PROBE

(75) Inventor: Michael G. Lowery, Wildwood, IL (US)

(73) Assignee: Abbott Diabetes Care Inc., Alameda, CA (US)

( * ) Notice: Subject to any disclaimer, the term of this patent is extended or adjusted under 35 U.S.C. 154(b) by 1544 days.

(21) Appl. No.: 10/823,073

(22) Filed: Apr. 13, 2004

(65) Prior Publication Data

US 2005/0226912 A1    Oct. 13, 2005

(51) Int. Cl.
*A61B 5/1455* (2006.01)
*A61K 9/00* (2006.01)
*A01N 25/34* (2006.01)

(52) U.S. Cl. .......................... 600/310; 424/400; 424/402

(58) Field of Classification Search .................. 600/344, 600/322, 310; 604/289; 424/443, 449, 400, 424/402; 428/40, 43; 132/319, 320
See application file for complete search history.

(56) References Cited

U.S. PATENT DOCUMENTS

| | | | |
|---|---|---|---|
| 3,598,123 A | 8/1971 | Zaffaroni | |
| 4,655,225 A | 4/1987 | Dahne et al. | |
| 4,758,434 A * | 7/1988 | Kydonieus et al. | 424/449 |
| 4,975,581 A | 12/1990 | Robinson et al. | |
| 5,008,110 A * | 4/1991 | Benecke et al. | 424/448 |
| 5,054,488 A * | 10/1991 | Muz | 600/344 |
| 5,348,003 A | 9/1994 | Caro | |
| 5,379,764 A | 1/1995 | Barnes et al. | |
| 5,402,777 A | 4/1995 | Warring et al. | |
| 5,402,778 A | 4/1995 | Chance | |
| 5,409,471 A * | 4/1995 | Atkinson et al. | 604/289 |
| 5,551,422 A | 9/1996 | Simonsen et al. | |
| 5,596,987 A | 1/1997 | Chance | |
| 5,655,530 A | 8/1997 | Messerschmidt | |
| 5,823,951 A | 10/1998 | Messerschmidt | |
| 5,830,136 A | 11/1998 | Delonzor et al. | |

(Continued)

FOREIGN PATENT DOCUMENTS

EP    0 272 918    6/1988

(Continued)

OTHER PUBLICATIONS

Bruulsema, et al., "Correlation between blood glucose concentration in diabetics and noninvasively measured tissue optical scattering coefficient". Optics Letters, vol. 22, No. 3., Feb. 1, 1997, pp. 190-192.

(Continued)

*Primary Examiner* — Eric Winakur
*Assistant Examiner* — Chu Chuan (JJ) Liu
(74) *Attorney, Agent, or Firm* — Edward J. Baba; Marcus T. Hunt; Bozicevic, Field & Francis LLP

(57) ABSTRACT

This invention provides an article of manufacture and method for controlling the application of a coupling agent, such as a silicone oil or mineral oil, on a surface of a tissue prior to contacting the tissue with an apparatus for non-invasive optical measurement of the concentration of an analyte. The article ensures that a specific quantity of the coupling agent is deposited in a uniform layer over the entire target area of the tissue, thereby enhancing both the optical signal and the repeatability of thermal and optical coupling with the components of the apparatus. The article comprises a backing and a layer of coupling agent on at least one major surface of the backing.

27 Claims, 4 Drawing Sheets

U.S. PATENT DOCUMENTS

| | | | |
|---|---|---|---|
| 5,919,476 A * | 7/1999 | Fischer et al. | 424/443 |
| 5,978,691 A | 11/1999 | Mills | |
| 6,016,435 A | 1/2000 | Maruo et al. | |
| 6,045,279 A * | 4/2000 | Follis | 401/6 |
| 6,106,852 A * | 8/2000 | Vineberg | 424/402 |
| 6,241,663 B1 | 6/2001 | Wu et al. | |
| 6,263,226 B1 | 7/2001 | Axelgaard et al. | |
| 6,526,298 B1 | 2/2003 | Khalil et al. | |
| 6,654,620 B2 | 11/2003 | Wu et al. | |
| 6,662,030 B2 | 12/2003 | Khalil et al. | |
| 6,662,031 B1 | 12/2003 | Khalil et al. | |
| 2002/0055671 A1 | 5/2002 | Wu et al. | |
| 2002/0110672 A1 * | 8/2002 | Muratore-Pallatino et al. | 428/195 |

FOREIGN PATENT DOCUMENTS

| | | |
|---|---|---|
| WO | 99/59464 | 11/1999 |

OTHER PUBLICATIONS

Bruulsema, et al., "Optical Properties of Phantoms and Tissue Measured *in vivo* from 0.9-1.3 μm using Spatially Resolved Diffuse Reflectance". SPIE, vol. 2979, 1997, pp. 325-334.

* cited by examiner

ARTICLE AND METHOD FOR APPLYING A COUPLING AGENT FOR A NON-INVASIVE OPTICAL PROBE

BACKGROUND OF THE INVENTION

1. Field of the Invention

This invention relates to the non-invasive determination of the concentration of an analyte, e.g., the concentration of glucose in blood, more particularly, an article and method for improving coupling between a subject and an apparatus having a sensor employing an optical probe.

2. Discussion of the Art

U.S. Pat. No. 6,241,663 describes the benefit of applying a coupling agent, such as silicone oil or mineral oil, on both the apparatus and the surface of the tissue of a subject prior to placing them in contact with each other for optical measurements. U.S. Pat. No. 6,241,663 shows that the use of a coupling agent between an optical probe and the tissue, e.g., skin, improves thermal coupling and decreases drift in the optical signal. Decrease in drift is highly desirable, especially in the case of small changes in optical signals encountered in the non-invasive determination of the concentration of analytes. However, U.S. Pat. No. 6,241,663 does not describe a method for controlling the amount of coupling agent applied to the surface of the tissue or the distribution of the coupling agent on the surface of the tissue. Typically, the coupling agent is deposited onto the surface of the tissue by means of a syringe. The thickness of the layer of coupling agent is not quantified, nor is a method for regulating the thickness of the layer of coupling agent and for ensuring the uniformity of the layer of coupling agent described. The thickness of the layer of coupling agent will affect the transmission of both light and heat between the optical probe and the tissue, thereby consequently affecting the optical signals measured. Consequently, test-to-test variations in the optical signals may result when the coupling agent exhibits test-to-test changes in thickness or distribution or both along the interface of the tissue and the optical probe. These random variations in the optical signal may hinder the calibration of the apparatus, and, consequently, adversely affect the measurement of the concentration of a biological analyte, such as glucose.

Contact of the optical probe and the skin leads to a unidirectional change in signal as a function of time, i.e., drift, even in the absence of changes in concentration of glucose. See Bruulsema, et al., Optical Properties of Phantoms and Tissue measured in vivo from 0.9-1.3 µm using Spatially Resolved Diffuse Reflectance, SPIE Vol., 2979, 1997, 325-334 and Bruulsema, et al., Correlation between blood glucose concentration in diabetics and noninvasively measured tissue optical scattering coefficient, OPTICS LETTERS, Vol. 22, no. 3, Feb. 1, 1997, 190-192. U.S. Pat. No. 4,975,581 describes such a drift and employs the first derivative of the spectrum to minimize it. This method of compensation does not address the cause of the problem. In fact, in a spatially resolved diffuse reflectance measurement taken on the skin, the drift of signal observed by Bruulsema was so large that statistical analysis of results was precluded.

The art shows methods of addressing the optical coupling issue by providing (a) media having known optical properties or (b) refractive index coupling media between the tissue and the optical probe. U.S. Pat. No. 5,596,987 and U.S. Pat. No. 5,402,778 describe methods for measuring optical properties of tissue. In particular, U.S. Pat. No. 5,596,987 discloses a spectrophotometric system including a spectrophotometer having a light source adapted to introduce radiation at an optical input port, a detector adapted to detect radiation that has migrated through a path from the input port to an optical detection port, and a processor adapted to evaluate changes between the introduced and the detected radiation. The system also includes an optical medium of a relatively large volume, forming photon escape preventing means, having selectable scattering and absorptive properties, positioning means adapted to locate the biological tissue of interest into the migration path to create a tissue-medium optical path, and processing means adapted to determine a physiological property of the tissue based on the detected optical property of the tissue-medium optical path and the scattering or absorptive properties of the optical medium. The photon escape preventing means includes an optical medium of a selectable optical property surrounding the tissue. The selectable optical property is an absorption or scattering coefficient. The medium has at least one optical property substantially matched to the selected optical property of the tissue. In one aspect, the optical coupling system includes an optical matching fluid that is contained within a flexible, optically transparent bag and disposed partially around the tissue being monitored and the input and detection ports of the system. The optical medium may include scattering material, such as solid particles having smooth, spherical surfaces, or styrofoam. The optical medium may include a liquid having selectable absorptive or scattering properties, such as an intralipid solution. The optical coupling medium may include a pliable solid having selectable scattering or absorption properties.

U.S. Pat. Nos. 5,655,530 and 5,823,951 describe an optical method for non-invasively measuring the concentration of an analyte, particularly blood analyte in blood. The method utilizes spectrographic techniques in conjunction with an improved optical interface between a sensor probe and a skin surface or tissue surface of the body containing the blood to be analyzed. An index-matching medium is disclosed to improve the interface between the sensor probe and the surface of the skin during spectrographic analysis.

The coupling agent in U.S. Pat. No. 6,241,663 is mainly used to improve the thermal and optical contact between the optical probe of the measuring apparatus and the skin. U.S. Pat. Nos. 5,655,530 and 5,823,951 describe the benefit of applying a refractive-index matching agent, such as fluorocarbons, water-based fluid mixtures, on both the non-invasive optical measuring device and the surface of the tissue prior to placing them into contact with each other for optical measurements. U.S. Pat. No. 5,596,987 describes a method that involves immersing the tissue in an optically matching coupling fluid. However, these patents do not describe a method for controlling the amount of coupling agent required or the distribution of the coupling agent on the surface of the tissue. U.S. Pat. Nos. 5,655,530; 5,823,951; and 5,596,987 do not quantify the thickness of the layer of coupling agent or describe a method for regulating the thickness of the layer of coupling agent or ensuring the uniformity of the layer of coupling agent. Too much coupling agent will lead to slippage of the measuring device with respect to tissue (e.g., skin), and generate motion artifacts in the measurements. Too little coupling agent will lead to incomplete coverage of the tissue (e.g., skin). Either of these factors will cause high variability in the results.

Accordingly, it would be desirable to provide an article and a method for applying a uniform layer of coupling agent over the surface of the tissue. It would also be desirable to provide an article and a method for applying a uniform layer of coupling agent over the surface of the tissue, wherein the uniform layer exhibits the same thickness from application to application.

SUMMARY OF THE INVENTION

In one aspect, the invention provides a method for applying a specified amount of a coupling agent, such as a silicone oil or mineral oil, to the surface of a tissue or a body part in order to facilitate thermal and optical coupling between the tissue or body part and an optical probe of a measuring apparatus that is brought in contact with the tissue for the purpose of performing a non-invasive determination of the concentration of an analyte in the tissue. The coupling agent can comprise any of the fluids described in U.S. Pat. Nos. 6,241,663 and 6,654,620, which have desirable coupling properties for this application.

In another aspect, the invention provides an article of manufacture for applying a coupling agent on a surface of a tissue prior to contacting the tissue with an apparatus for measuring the optical properties of the tissue and determining the concentration of analyte in the tissue. Such apparatus are described in U.S. Pat. Nos. 6,662,030; 6,662,031; 6,526,298; WO 99/59464. The article ensures that a specific quantity of the coupling agent is deposited in a uniform layer over the entire target area of the tissue, thereby enhancing both the optical signal and the repeatability of thermal and optical coupling of the tissue with the optical probe of the apparatus.

In one embodiment, the article comprises (a) a backing and (b) a layer of coupling agent on at least one major surface of the backing. In this embodiment, the material of the backing must not absorb an excessive amount of the coupling agent. In an alternative embodiment, the article comprises (a) a backing, (b) a layer of fibrous or non-fibrous material overlying the backing, and (c) a layer of coupling agent on the major surface of the layer of fibrous or non-fibrous material not in contact with the backing. In the alternative embodiment, the layer of fibrous or non-fibrous material prevents the coupling agent from being absorbed by the backing. In either embodiment, the method involves the steps of (1) applying a specified amount of a coupling agent to the surface of a tissue or a body part; (2) bringing an optical measuring device in contact with the tissue or the body part, wherein said coupling agents enhances optical and thermal coupling between the device and the tissue or the body part; and (3) performing a non-invasive determination of the concentration of an analyte in the tissue or the body part.

The article of this invention enables application of a layer of the coupling agent in a uniform, repeatable thickness on the surface of the tissue, thereby improving the consistency of test results using the apparatus. The article makes it possible to regulate the thickness of the layer of the coupling agent on the surface of the tissue, thereby allowing users to determine which thickness yields the best test results. The article enables one to select the best thickness of the layer of the coupling agent according to the condition of the surface of the tissue. Test results can thus be optimized according the degree of roughness, firmness, and dryness of the tissue, and density of hair.

DETAILED DESCRIPTION

As used herein the term "apparatus" means a device suitable for measuring the concentration of an analyte in tissue non-invasively. The term "optical probe" means that portion of the apparatus that introduces optical signals into the tissue and collects optical signals from the tissue. The coupling agent is placed between the optical probe and the tissue. The term "sensor" means that portion of the apparatus that is involved in detecting the optical signal exiting from the tissue.

Figure 1A:
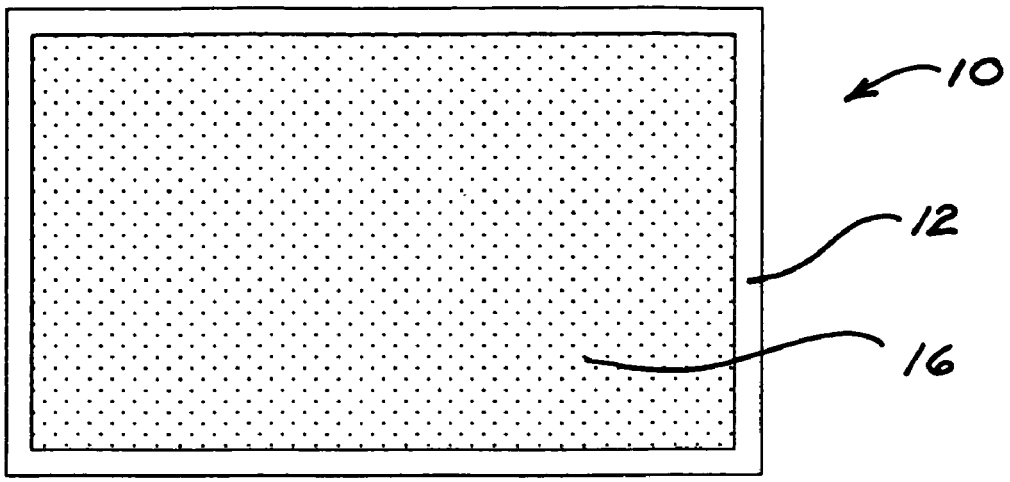
FIG. 1A is a top plan view of an article suitable for use in this invention.
Figure 1B:
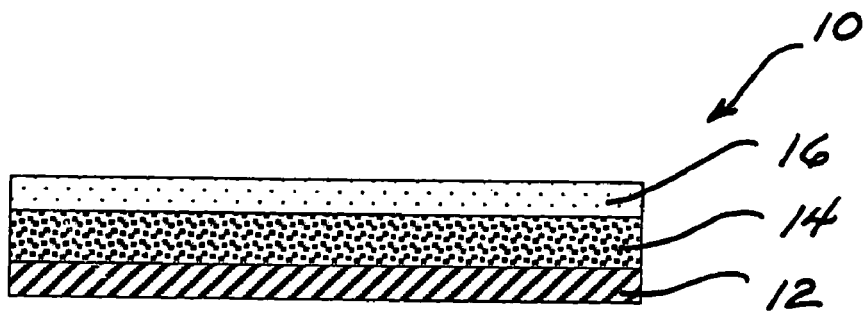
FIG. 1B is a cross-sectional view of the article of FIG. 1A, taken along line 1B-1B, showing an article having three layers.

FIGS. 1A and 1B illustrate a preferred embodiment of the article 10 of this invention. The article 10 comprises a backing layer 12 supporting a substrate layer 14 on one major surface of which is a layer of a coupling agent 16.

The backing layer 12 provides the essential shape of the surface of the article 10. The backing layer 12 is impermeable to the coupling agent. The backing layer 12 is preferably thin and flexible to allow the article 10 to conform to surfaces of the tissue that are not flat. Alternatively, the backing layer 12 can be thick and rigid to function as a type of "stamping" device. The type of backing layer preferred can be selected by routine experimentation to deliver the optimal combination of accurate test results and ease of use. As used herein, "routine experimentation" means running a series of experiments and selecting a satisfactory result, preferably the optimal result, from the experiments in the series. Typically, no more than about ten experiments need to be run to select a satisfactory result. Even if more than ten experiments are carried out, the time involved to carry them out would not be extensive, typically less than about two weeks.

Representative examples of materials that are suitable for the backing layer include, but are not limited to, metals, rubber, such as, for example, hard rubber, soft rubber, plastics, and other polymeric materials. It is preferred that the material of the backing layer not be capable of absorbing the coupling agent. The material of the backing layer can be flexible or rigid. Rigid materials, e.g., hard rubber, can be used when the article operates as by stamping. Flexible materials, e.g., soft rubber, can be used when the article operates as a patch. It is preferred that the surface of the backing layer in contact with the coupling agent be non-porous. It is preferred that the dimensions of the backing layer be such that the area of the backing layer at least surround area to contact the optical probe, and it is more preferred that the area of the backing layer be greater than the area to contact the optical probe to allow for a margin of error in the event of imperfect placement of the article on the skin.

In a preferred embodiment, which includes a substrate layer, the substrate layer 14 (typically having a thickness of less than 1 mm) is adhered to the backing layer 12. The substrate layer 14 provides the surface upon which the layer of coupling agent 16 is deposited. In an alternative embodiment, the substrate layer 14 can be omitted, provided that the backing layer 12 can perform the function of the substrate layer. The substrate layer 14 can be a porous or a non-porous material. It is preferred that the substrate layer 14 be porous, so that the coupling agent can be better retained by the article during storage, shipping, and handling prior to use.

A flexible, non-porous backing layer 12 can be formed from "Scotch" Magic tape. A flexible, porous substrate layer 14 can be formed from "Post-it" note stock. One of ordinary skill in the art of depositing the coupling agent can select an appropriate material for the substrate layer 14, such that the coupling agent can be deposited uniformly on one major surface of the substrate layer 14 and remain fixed until the article 10 is used to apply the coupling agent to the target tissue. The substrate layer 14 must also be capable of allowing a uniform layer of coupling agent to be transferred onto the target tissue during the application step.

On the substrate layer 14 in the preferred embodiment is a layer of coupling agent 16, which is preferably a thin film (typically having a thickness of less than 100 μm, preferably from about 7 μm to about 20 μm, more preferably from about 7 μm to about 11 μm) having substantially uniform thickness. The thickness of the layer of coupling agent 16 can be selected by means of routine experimentation such that the preferred amount of coupling agent is transferred to the target tissue upon contact. The preferred amount of coupling agent on the tissue can be determined by routine experimentation to achieve satisfactory test results with the use of the non-invasive apparatus, such as, for example, the apparatus described in U.S. Pat. No. 6,241,663. The amount of coupling agent that is eventually applied to the tissue is determined by routine experimentation. The preferred amount of coupling agent can vary from person to person and from site to site on the human body, depending on such factors as roughness, firmness, and dryness of skin, and the density of hair. For example, a higher quantity of coupling agent may be needed to displace all the air spaces surrounding thick strands of hair. One of ordinary skill in the art can select a suitable method to deposit a specific amount of coupling agent on the substrate layer 14. Two representative processes include rod coating and screen-printing. When a porous substrate layer 14 is used, a sufficient amount of coupling agent must be deposited to saturate the material of the substrate layer 14 and leave a film of specified thickness on its surface. A similar procedure is applicable when a substrate layer is not used. Representative examples of coupling agents suitable for use in this invention can be selected from the group consisting of mineral oil, silicone oil, dimethyl siloxane, fluorocarbons, and glycols. Suitable coupling agents are also listed in U.S. Pat. No. 6,241,663, incorporated herein by reference.

Figure 2:
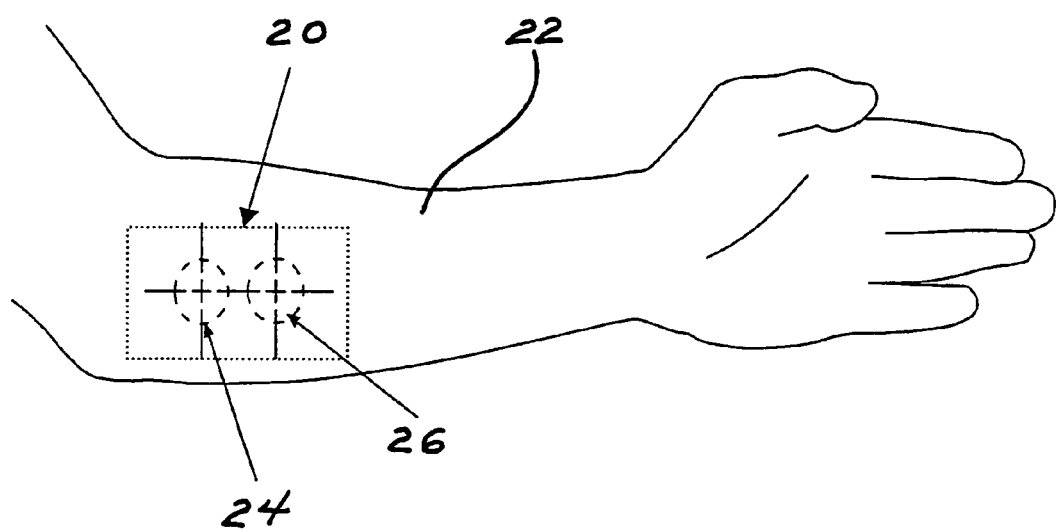
FIG. 2 illustrates the target region on human tissue for contact with the article of this invention.

FIG. 2 illustrates a target region 20 for the article 10 on the left forearm 22. In FIG. 2, two circular contact sites 24 and 26 are shown on the left forearm 22. These contact sites 24, 26 coincide with the two circular sensors of an optical probe (not shown). The layer of coupling agent 16 is preferably rectangular in shape and has a sufficiently large area to cover the two contact sites 24 and 26. The rectangular layer 16 preferably has dimensions of approximately 2 inches×1 inch. The shape of the layer 16 need not be rectangular; the layer 16 may also have other shapes, such as for example, elliptical, oval, circular, polygonal, or any shape having an area equal to or greater than area of probe that will be in contact with the surface of the skin so that the coupling agent will at least cover the area of the surface of the skin that will contact the sensor(s) of the optical probe. The area of the layer 16 preferably ranges from about 10 cm² to about 40 cm².

Figure 3A:
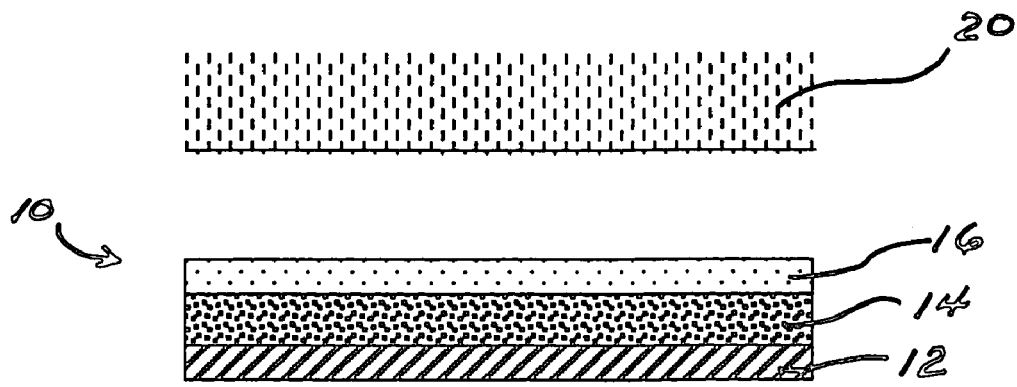
FIGS. 3A, 3B, and 3C illustrate the steps involved in a method of applying a layer of coupling agent to the surface of human tissue by means of the article of this invention.
Figure 3B:
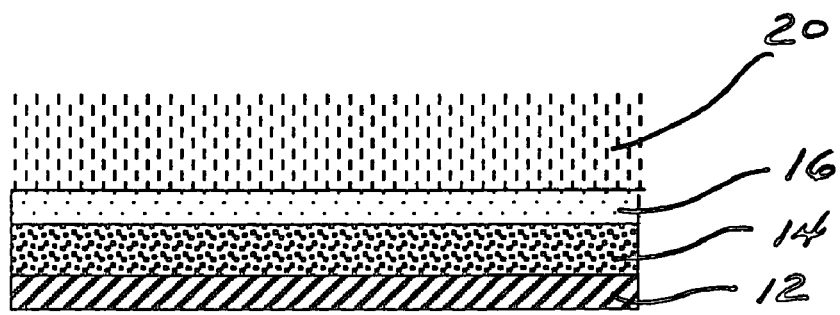
Figure 3C:
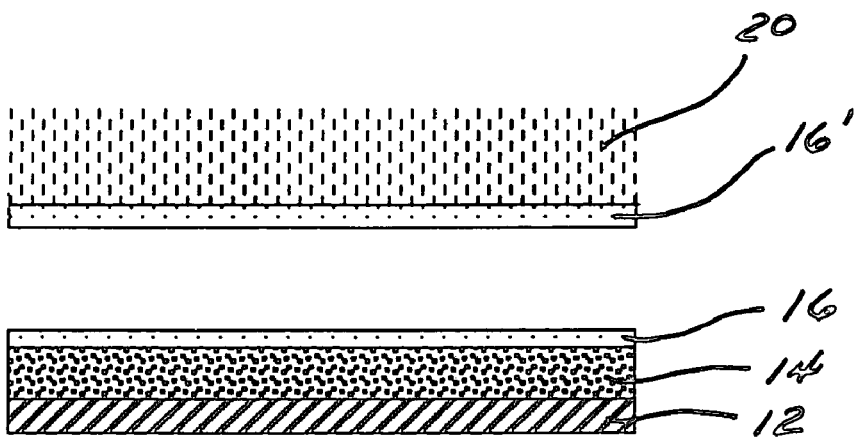

FIGS. 3A, 3B, and 3C show the steps needed to apply the coupling agent to the surface of the tissue or a body part. In FIG. 3A, the layer of coupling agent 16 of the article 10 is brought into close proximity and aligned with the surface of the target region 20 of the tissue or the body part. In FIG. 3B, the layer of coupling agent 16 is placed in contact with the target region 20 of the tissue or the body part. A low level of pressure can be exerted manually on the article 10 to bring all regions of the layer of coupling agent 16 into contact with the tissue or the body part. In FIG. 3C, the article 10 is removed and the appropriate amount of coupling agent 16' has been transferred to the surface of the tissue or the body part. The coupling agent transferred has a substantially uniform, specified thickness (typically less than 100 μm) throughout the entire contact region. The coated tissue in FIG. 3C is ready for use with the measuring apparatus.

The relationship of the thickness of the layer of coupling agent to the rate of heat conduction between the sensor(s) and surface of the tissue can be approximated by means of the Fourier equation:

$$q = [k/x][T_s - T_t]$$

where q represents the flux of heat conduction through the medium, e.g., coupling agent, air, in W/m²;

k represents the thermal conductivity of the medium, e.g., coupling agent, air, in W/m·°C.;

x represents the thickness or length of the layer of the medium, e.g., coupling agent, air, in meters;

$T_s$ represents the temperature of the surface of the sensor of the optical probe (°C.); and $T_t$ represents the temperature of the surface of the tissue (°C.).

In this equation, the rate of heat conduction between the surface of the sensor of the optical probe and the treated surface of the tissue is inversely proportional to the thickness of the layer of coupling agent ($x_{ca}$). Therefore, in order to achieve a repeatable rate of and uniform amount of heat conduction across the interface of the sensor of the optical probe and the surface of the tissue, a repeatable and uniform thickness of coupling agent is needed. Furthermore, another purpose of the coupling agent is to substantially increase the rate of heat conduction, as compared with an untreated surface of tissue. In the case of an untreated surface of tissue, the coupling agent is replaced by an air gap at the interface of the sensor of the optical probe and the surface of the tissue, on account of the uneven nature of the surface of the tissue, e.g., skin. The rate of heat conduction between the sensor of the optical probe and an untreated tissue surface can also be approximated by the Fourier equation q of air=$[k_a/x_a][T_s - T_t]$, where $k_a$ is the thermal conductivity (W/m·°C.) of air and $x_a$ is the average air gap length (meter) between the sensor of the optical probe and the surface of the tissue. The flux of heat conduction in the case of an air gap will depend on the thermal conductivity of air and the dimensions of the air gap. Air gaps may vary in size according to such factors as the skin topography (roughness, hair density, etc.).

Although the thermal conductivity of the coupling agent ($k_{ca}$) will be greater than that of air, i.e., $k_{ca} > k_a$, the thickness of the layer of coupling agent ($x_{ca}$) will likely be greater than the lengths of the air gaps, i.e., $x_{ca} > x_a$, consequently offsetting the benefit of a higher conductivity value. If the thickness of the layer of coupling agent, $x_{ca}$, is too great, then the ratio $[k_{ca}/x_{ca}]$ may not substantially increase, compared to the ratio $[k_a/x_a]$. Therefore, in order for the coupling agent to increase the rate of heat transfer relative to that of an untreated surface, the ratio $[k_{ca}/x_{ca}]$ must be greater than $[k_a/x_a]$. The thermal conductivity of the coupling agent is greater than that of air (i.e., $k_{ca} > k_a$), which helps achieve this improvement. However, if the thickness of the coupling agent layer is greater than the average gap length of the air that was displaced (i.e., $x_{ca} > x_a$), then it is possible for the ratio $[k_{ca}/x_{ca}]$ to be less than $[k_a/x_a]$, with the result that the rate of heat conduction between the sensor of the optical probe and the surface of the tissue would actually decrease relative to the rate of heat conduction between the sensor of the optical probe and the untreated surface of the tissue. This would defeat the purpose of applying the coupling agent to improve the efficiency of heat transfer. Consequently, the improvement in heat conduction achieved by introducing the coupling agent may be marginal or non-existent, i.e., q of coupling agent≈q of air. Too much coupling agent will lead to slippage of the measuring device with respect to the tissue (e.g., skin), and generate motion artifacts in the measurements. Too little coupling agent will lead to incomplete coverage of the tissue (e.g., skin) and hence incomplete coupling of the sensor of the optical probe to the surface of the tissue. Either of these factors will cause high variability in the results. Additionally, the use of syringes and droppers to apply the coupling agent may lead to dropping fluid on the floor, which renders floors slippery, and hazardous, particularly when the coupling agent is silicon oil. Thus, while there is a need to apply coupling agents to the tissue to improve the results of a non-invasive optical measurement, there is yet a further need of applying a uniform layer of this coupling agent on the tissue to obtain consistent results. Additionally, there is a desire to have a self-contained device for applying the coupling agent in order to prevent spillage of the coupling agent. Both of these needs are met by the article and method of this invention.

The invention provides several advantages relative to conventional methods of applying a coupling agent, as described in U.S. Pat. No. 6,241,663:

1) The article enables application of the coupling agent in a uniform, repeatable thickness on the surface of the tissue, thereby improving the consistency of test results using a non-invasive monitoring apparatus. As used herein, "uniform" means having little or no variation or fluctuation; "repeatable thickness" means a thickness that can be duplicated from one application to another.

2) The article makes it possible to regulate the thickness of coupling agent on the surface of the tissue, thereby allowing users to determine which thickness yields the best test results.

3) The article enables one to select the best thickness of the coupling agent according to the condition of the surface of the tissue. Test results can thus be optimized according the degree of roughness, firmness, and dryness of tissue, and density of hair.

The method and article of this invention can be used with the apparatus described in U.S. Pat. Nos. 6,662,030; 6,662,031; 6,526,298; and WO 99/59464. The method and article of this invention can also be used with the measurement methods and devices described in U.S. Pat. Nos. 4,975,581; 5,379,764; 4,655,225; 5,348,003; 5,551,422; 5,978,691; 6,016,435. Thus, the method of this invention can be used with any non-invasive optical measurement for the determination of concentration of analytes in human tissue. These non-invasive measurements include diffuse reflectance measurements, localized reflectance measurements, time domain measurements, frequency domain measurement, photoacoustic measurements, and optical coherence tomography measurements. The method is applicable whenever a measuring device is brought in contact with the tissue, in order to improve optical and thermal coupling between the measuring device and the tissue, and consequently improve the measurement precision. Because some of the imprecision in optical measurement of tissue results from the non-specific change in optical signal as a function of time, known as drift, some of the following examples illustrate the ability of the method of this invention to decrease signal drift.

The method and article of this invention can be used in conjunction with apparatus having an optical probe for the non-invasive determination of the concentrations of analytes in the human body in order to improve the precision of measurement. Examples of analytes whose concentrations can be determined by the method and the article of this invention include, but are not limited to, glucose, hemoglobin, glycated hemoglobin, triglycerides, cholesterol and other metabolites, drugs, or hormones that affect the optical properties of human tissue.

EXAMPLES

The following non-limiting examples further illustrate this invention.

Example 1

This example illustrates a method for constructing the article of this invention. A rectangular article for applying a coupling agent was made by using readily available materials. The article had dimensions of approximately 3 inches×2 inches and comprised three layers, as illustrated in FIGS. 1A and 1B. A porous substrate layer was formed from a sheet of 630 Post-It® paper (3M, St. Paul, Minn.). The paper had a thickness of approximately 0.1 mm and was manually cut into sections having surface dimensions of 3 inches×2 inches. A backing layer comprising conventional Scotch™ non-permeable tape having a layer of adhesive on one major surface thereof was adhered to one side of the substrate layer manually, whereby the substrate layer completely covered the surface of the backing layer. This laminated unit was sufficiently mechanically flexible to conform to the shape of the surface of a forearm. The coupling agent selected was a viscous silicone oil (Aldrich Chemical Co., Cat. No. 37,839-9, Poly (dimethylsiloxane) 200® fluid). The silicone oil had a refractive index of 1.404, a thermal conductivity of about 0.15 W/m○° C., a density of about 0.97 g/mL, and a viscosity of 1000 cSt. The coupling agent was coated onto the substrate layer by means of a conventional wire-rod coating device (Resource I, Jamesburg, N.J., Mach. No. 1010A). Rod No. 34 was installed in the coating device to spread approximately 220 µL of oil completely and uniformly onto the substrate layer. After the coating step, the article was allowed to remain in place for at least 10 minutes at room temperature to allow the oil to completely saturate the substrate layer and the adhesive material in the backing layer. Following saturation, the film of oil had a thickness of approximately 17 µm to 18 µm on the surface of the substrate layer.

Example 2

This example illustrates application of a uniform layer of coupling agent to the surface of a tissue. Five articles of the type described in Example 1 were constructed for testing on the left forearm of a volunteer. The weight of each article was first recorded on a balance scale for reference. The first article was placed upon the forearm region shown in FIG. 2 and gently pressed to ensure that the entire coated surface contacted the skin of the forearm. The article was then immediately peeled away from the skin, and its weight was again recorded on the balance scale. The difference in weight was used to determine the volume and average thickness of the layer of silicone oil transferred to the surface of the skin. On the surface of the skin, the silicone oil appeared to be uniformly distributed within the 3-inch×2-inch rectangular region. The silicone oil was then washed off the surface of the skin, and the test was repeated by using the remaining four articles. The calculated amount of silicone oil transferred to the forearm during each test is tabulated in Table 1, demonstrating a high degree of repeatability. The average thickness of the layer of oil on the skin was calculated to be 10.8 μm, with a standard deviation of 0.4 μm for the five tests.

TABLE 1

Silicone Oil Transferred to the Skin of the Forearm (Coating Rod No. 34)

| Test No. | Volume Transferred (μL) | Thickness Transferred (μm) |
|---|---|---|
| 1 | 42.8 | 10.9 |
| 2 | 40.2 | 10.3 |
| 3 | 44.4 | 11.3 |
| 4 | 40.7 | 10.4 |
| 5 | 42.8 | 10.9 |
| Average (±σ) | 42.2 (±1.7) | 10.8 (±0.4) |

Example 3

This example illustrates how the invention can be used to regulate the thickness of the coupling agent. Five additional articles were constructed according to the procedure described in Example 1, except that Rod No. 28 was substituted in the coating device in order to deposit a smaller volume of silicone oil onto the substrate layer. By using Rod No. 28, the volume of oil deposited was reduced from about 220 μL to about 190 μL. Each of the coated articles was tested sequentially on the skin of the forearm by using the procedure described in Example 2. The amounts of silicone oil transferred to the surface of the skin are tabulated in Table 2. Compared to the results in Table 1, the average thickness of oil on the skin was reduced from about 10.8 μm to about 7.4 μm.

TABLE 2

Silicone Oil Transferred to the skin of the Forearm (Coating Rod No. 28)

| Test No. | Volume Transferred (μL) | Thickness Transferred (μm) |
|---|---|---|
| 1 | 27.6 | 7.1 |
| 2 | 28.7 | 7.3 |
| 3 | 28.7 | 7.3 |
| 4 | 29.2 | 7.4 |
| 5 | 30.3 | 7.7 |
| Average (±σ) | 28.9 (±1.0) | 7.4 (±0.2) |

Example 4

Figure 4A:
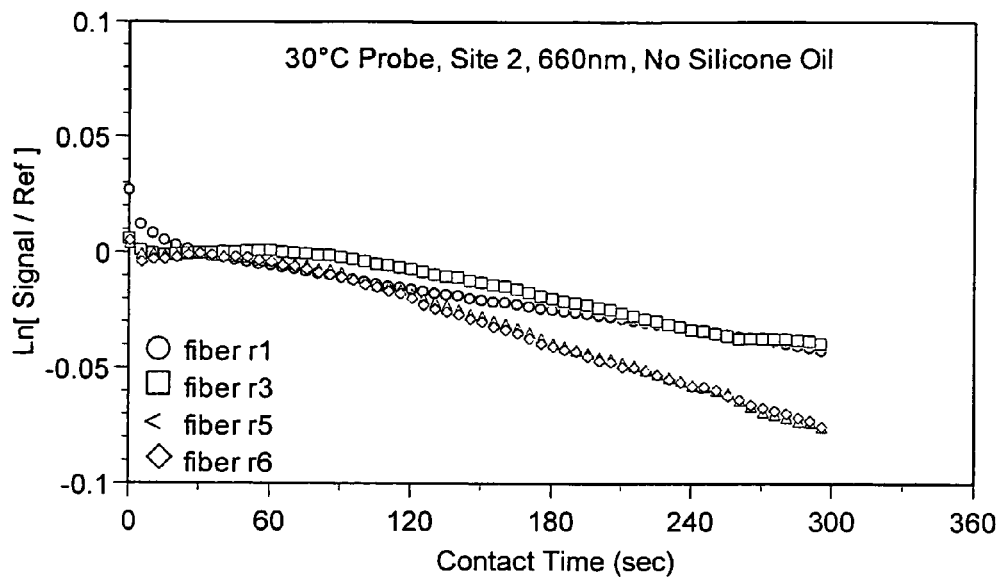
FIG. 4A is a plot showing the logarithm of signal as a function of time, with no coupling agent present.

This example illustrates the use of the invention with the apparatus described in WO 99/59464. The invention was tested on the left forearm of a volunteer to record the change in optical signals. FIG. 2 illustrates the contact sites 24, 26 for the two circular sensors of the optical probe. The sensors were initially tested on skin of the forearm for a period of five minutes, during which time the temperature of the sensors of the optical probe was maintained at 30° C. In each sensor, optical signals were recorded at 5-second intervals at four collection fibers (see optical fibers r1, r3, r5 and r6 in FIG. 4 of WO 99/59464). The source of light had a wavelength of 660 nm. The measurements at site 26 were chosen for plotting in FIG. 4A. In FIG. 4A, the logarithmic values of the four optical signals corresponding to the four collection fibers were plotted as a function of time. The results show a downward drift in signal strength during the 5-minute test. The drift was caused by an inefficient optical/thermal coupling between the probe and the untreated skin.

Figure 4B:
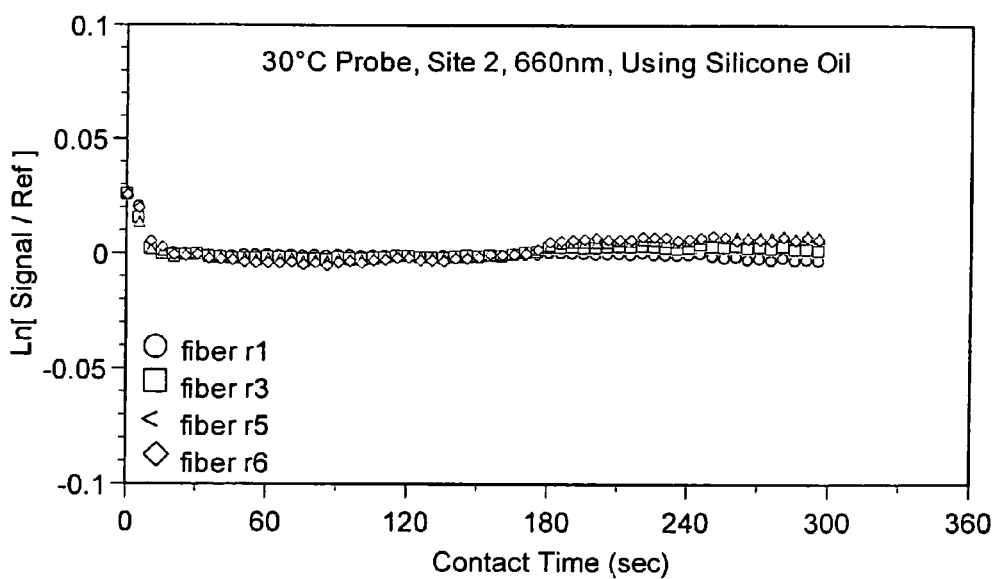
FIG. 4B is a plot showing the logarithm of signal as a function of time, with coupling agent present.

A second test (on the same region of the forearm) involving both the article of this invention and the apparatus of WO 99/59464 was initiated approximately 30 minutes after the first test. The 30-minute period enabled the tissue of the forearm to return to its natural state after interaction with the sensor. The article was constructed according to Example 1, and comprised a 3-inch×2-inch rectangular article having a layer of silicone oil as the coupling agent. The application step in Example 2 was repeated to transfer a layer of silicone oil having a thickness of approximately 11 μm from the layer of silicone oil of the article to the region of the forearm shown in FIG. 2. Immediately following the application step, the apparatus was brought into contact with the layer of oil on the skin and the test protocol was repeated. FIG. 4B illustrates the results for the four optical signals at site 26. The optical signals in FIG. 4B exhibited much less drift during the 5-minute test as compared with the optical signals in FIG. 4A. It is assumed that the reduction in drift was caused by an improvement in the optical/thermal coupling between the sensor of the optical probe and the surface of the skin.

The invention is intended for use with a non-invasive optical probe, such as, for example, the type described in WO 99/59464, as a means for applying a beneficial layer of coupling agent to the surface of the target tissue prior to testing. A disposable article can be applied to the target body site, such as the volar forearm, as part of a pre-conditioning step before using the non-invasive optical probe. Furthermore, the disposable article can be offered in several variations (shape, coupling agent, thickness of layer, etc.) to achieve the best test results for different body sites and skin conditions.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. An article for applying a coupling agent to a surface of a tissue or a body part, the article comprising:
   a backing, wherein the backing comprises a non-permeable material, the backing comprising a flat major surface on a skin-contacting side of the article; and
   a layer of coupling agent deposited over the flat major surface of the backing on the skin-contacting side of the article such that the layer of coupling agent provides a surface on the article for contacting the tissue or body part;
   wherein only the layer of coupling agent is over the flat major surface of the backing on the skin-contacting side of the particle;
   wherein the article comprising the backing and the layer of coupling agent is configured such that a predetermined amount of the layer of coupling agent is uniformly and usably transferable to the surface of the tissue or the body part upon removal of the article comprising the backing and the layer of coupling agent from the tissue or the body part, wherein the predetermined amount of the layer of coupling agent enhances optical and thermal coupling between the tissue or the body part and a separate measuring device including an optical probe.

2. The article of claim 1, wherein the coupling agent is selected from the group consisting of mineral oil, silicon oil, dimethyl siloxane, fluorocarbons, and glycols.

3. The article of claim 1, wherein a thickness of the layer of coupling agent over the backing is less than about 100 μm.

4. The article of claim 1, wherein a thickness of the coupling agent over the backing is from about 7 μm to about 20 μm.

5. The article of claim 1, wherein the area of the backing is from about 10 cm² about 40 cm².

6. The article of claim 1, wherein the backing has an area greater than an area of the layer of coupling agent.

7. A method for improving the precision of a non-invasive optical measurement, said method comprising:
   providing an article comprising:
      a backing, wherein the backing comprises a non-permeable material, the backing comprising a flat major surface on a skin-contacting side of the article; and
      a layer of coupling agent deposited over the flat major surface of the backing on the skin-contacting side of the article, the layer of coupling agent providing a surface on the article for contacting a tissue or a body part;
      wherein only the layer of coupling agent is over the flat major surface of the backing on the skin-contacting side of the article;
   coupling the article comprising the backing and the layer of coupling agent to the surface of the tissue or the body part such that all regions of the layer of coupling agent contact the tissue or the body part and remain fixed to the tissue or the body part until peeled away from the tissue or the body part;
   removing the article comprising the backing and the layer of coupling agent from the surface of the tissue or the body part after all regions of the layer of coupling agent contact the tissue or body part by peeling the fixed article off the tissue or the body part, wherein upon the removing of the article, a specified amount of the layer of coupling agent is usably transferred to the surface of the tissue or the body part;
   bringing an optical measuring device in contact with the usably transferred coupling agent and said tissue or said body part, wherein said usably transferred coupling agent enhances optical and thermal coupling between said device and said tissue or said body part; and
   performing a non-invasive determination of the concentration of an analyte in said tissue or said body part.

8. The method of claim 7, wherein said optical measurement is one of diffuse reflectance measurements, localized reflectance measurements, time domain measurements, frequency domain measurement, photoacoustic measurements or optical coherence tomography measurements.

9. The method in claim 7, wherein said analyte is selected from the group consisting of glucose, hemoglobin, glycated hemoglobin, triglycerides, and cholesterol.

10. The method in claim 7, wherein the layer of coupling agent is uniform.

11. The article of claim 1, wherein the layer of coupling agent is uniform.

12. The method in claim 7, wherein the coupling of the article to the surface of the tissue or the body part comprises:
   positioning the article on the tissue or the body part; and
   applying pressure to the entire backing to bring all regions of the layer of coupling agent into contact with the tissue or the body part.

13. An article for applying a coupling agent to a surface of a tissue or a body part, the article comprising:
   a backing comprising adhesive material on a flat major surface of the backing;
   a layer of coupling agent over the flat major surface of the backing; and
   a porous substrate layer adhered to the flat major surface of the backing by the adhesive material and interposed between the backing and the layer of coupling agent;
   wherein the adhesive material and holes in the porous substrate layer are saturated by the coupling agent;
   wherein the article comprising the backing, the substrate layer, and the layer of coupling agent is configured such that a predetermined amount of the layer of coupling agent is uniformly and usably transferable to the surface of the tissue or the body part upon removal of the article comprising the backing, the substrate layer, and the layer of coupling agent from the tissue or the body part, wherein the predetermined amount of the layer of coupling agent enhances optical and thermal coupling between the tissue or the body part and a separate measuring device including an optical probe.

14. The article of claim 13, wherein the coupling agent is selected from the group consisting of mineral oil, silicon oil, dimethyl siloxane, fluorocarbons, and glycols.

15. The article of claim 13, wherein the backing comprises a non-permeable material.

16. The article of claim 13, wherein a thickness of the layer of coupling agent over the backing is less than about 100 μm.

17. The article of claim 13, wherein a thickness of the coupling agent over the backing is from about 7 μm to about 20 μm.

18. The article of claim 13, wherein the area of the backing is from about 10 cm² about 40 cm².

19. The article of claim 13, wherein the backing has an area greater than an area of the layer of coupling agent.

20. The article of claim 13, wherein the substrate layer comprises a fibrous material.

21. The article of claim 13, wherein the substrate layer comprises a non-fibrous material.

22. The article of claim 13, wherein the layer of coupling agent is uniform.

23. A method for improving the precision of a non-invasive optical measurement, said method comprising:
   providing an article comprising:
      a flat backing comprising adhesive material on a major surface of the backing;
      a layer of coupling agent over the major surface of the backing, the layer of coupling agent providing a surface on the article for contacting a tissue or a body part; and
      a porous substrate layer adhered to the major surface of the backing by the adhesive material and interposed between the backing and the layer of coupling agent;
      wherein the adhesive material and holes in the porous substrate layer are saturated by the coupling agent;
   coupling the article comprising the backing, the substrate layer, and the layer of coupling agent to the surface of the tissue or the body part such that all regions of the layer of coupling agent contact the tissue or the body part;
   removing the article comprising the backing, the substrate layer, and the layer of coupling agent from the surface of the tissue or the body part, wherein upon the removing of the article, a specified amount of the layer of coupling agent is usably transferred to the surface of the tissue or the body part;
   bringing an optical measuring device in contact with the usably transferred coupling agent and said tissue or said body part, wherein said usably transferred coupling agent enhances optical and thermal coupling between said device and said tissue or said body part; and
   performing a non-invasive determination of the concentration of an analyte in said tissue or said body part.

24. The method of claim 23, wherein said optical measurement is one of diffuse reflectance measurements, localized reflectance measurements, time domain measurements, frequency domain measurement, photoacoustic measurements or optical coherence tomography measurements.

25. The method in claim 23, wherein said analyte is selected from the group consisting of glucose, hemoglobin, glycated hemoglobin, triglycerides, and cholesterol.

26. The method in claim 23, wherein the layer of coupling agent is uniform.

27. The method in claim 23, wherein the coupling of the article to the surface of the tissue or the body part comprises:
    positioning the article on the tissue or the body part; and
    applying pressure to the entire backing to bring all regions of the layer of coupling agent into contact with the tissue or the body part.

\* \* \* \* \*